(12) United States Patent
Cornell et al.

(10) Patent No.: US 10,980,639 B2
(45) Date of Patent: Apr. 20, 2021

(54) IMPLANTS THAT FACILITATE TISSUE EXPANSION

(71) Applicant: Augmenta, LLC, Houston, TX (US)

(72) Inventors: Robert J. Cornell, Houston, TX (US); David J. Nichols, Bullard, TX (US); Hans A. Mische, Grey Eagle, MN (US)

(73) Assignee: Augmenta, LLC, Houston, TX (US)

( * ) Notice: Subject to any disclaimer, the term of this patent is extended or adjusted under 35 U.S.C. 154(b) by 39 days.

(21) Appl. No.: 16/238,821

(22) Filed: Jan. 3, 2019

(65) Prior Publication Data

US 2020/0022812 A1 Jan. 23, 2020

Related U.S. Application Data

(60) Provisional application No. 62/779,825, filed on Dec. 14, 2018, provisional application No. 62/702,062, filed on Jul. 23, 2018.

(51) Int. Cl.
*A61F 2/26* (2006.01)

(52) U.S. Cl.
CPC ........ *A61F 2/26* (2013.01); *A61F 2220/0008* (2013.01); *A61F 2250/0018* (2013.01); *A61F 2250/0019* (2013.01); *A61F 2250/0025* (2013.01); *A61F 2250/0037* (2013.01); *A61F 2250/0053* (2013.01); *A61F 2250/0071* (2013.01); *A61F 2250/0078* (2013.01)

(58) Field of Classification Search
CPC ......... A61F 2/02; A61F 2/26; A61F 2005/411
USPC .................................................... 600/38–40
See application file for complete search history.

(56) References Cited

U.S. PATENT DOCUMENTS

| | | | |
|---|---|---|---|
| 1,383,944 A | 7/1921 | Hart | |
| 2,899,957 A | 11/1957 | Briggs | |
| 3,893,456 A | 7/1975 | Small et al. | |
| 3,987,789 A | 10/1976 | Timm et al. | |
| 4,204,530 A | 5/1980 | Finney | |
| 4,483,331 A | 11/1984 | Trick | |
| 4,523,584 A | 6/1985 | Yachia et al. | |
| 4,589,405 A | 5/1986 | Hemmeter | |
| 4,602,625 A | 7/1986 | Yachia et al. | |
| 4,669,456 A | 6/1987 | Masters | |
| 5,445,594 A † | 8/1995 | Elist | |

(Continued)

FOREIGN PATENT DOCUMENTS

WO 1986001398 A1 3/1986

OTHER PUBLICATIONS

Int'l Search Report & Written Opinion (PCT/US2019/042782), dated Oct. 3, 2019.

(Continued)

*Primary Examiner* — John P Lacyk
(74) *Attorney, Agent, or Firm* — Gregory L Porter; Hunton Andrews Kurth LLP

(57) ABSTRACT

The invention pertains to implants that facilitate tissue expansion while not substantially inhibiting normal anatomical movement. The implants may be made of different materials or made in different configurations such that such that a measured property at a first location on said implant is different than said same measured property at a second location on said implant. In one particular embodiment the implants may be a cosmetic penile implant.

22 Claims, 13 Drawing Sheets

(56) References Cited

U.S. PATENT DOCUMENTS

| | | | |
|---|---|---|---|
| 5,512,033 | A | 4/1996 | Westrum, Jr. et al. |
| D376,011 | S | 11/1996 | Nunokawa |
| 5,669,870 | A † | 9/1997 | Elist |
| 5,899,849 | A † | 5/1999 | Elist |
| 6,015,380 | A | 1/2000 | Subrini |
| D462,770 | S † | 9/2002 | Elist |
| 6,475,137 | B1 † | 11/2002 | Elist |
| 6,537,204 | B1 † | 3/2003 | Elist |
| 7,572,221 | B2 † | 8/2009 | Atala |
| 8,986,193 | B1 † | 3/2015 | Elist |
| 9,504,573 | B1 † | 11/2016 | Elist |
| 9,877,835 | B1 | 1/2018 | Loria |
| 10,350,070 | B2 † | 7/2019 | Elist |
| 2003/0220539 | A1* | 11/2003 | George ............ A61F 2/26 600/40 |
| 2014/0031619 | A1 | 1/2014 | Moon |
| 2017/0020700 | A1 | 1/2017 | Bienvenu et al. |

OTHER PUBLICATIONS

Elist et al., "A Single-Surgeon Retrospective and Preliminary Evaluation of the Safety and Effectiveness of the Penuma Silicon Sleeve Implant . . . ", J. Sex. Med (2018), pp. 1216-1223.

Elist et al., "Correction of retractile penis with subcutaneous soft silicon penile implant", published online at https://doi.org/10.1038/s41443-019-0174-3 (Aug. 5, 2019).

\* cited by examiner
† cited by third party

SECTION A-A

SECTION B-B

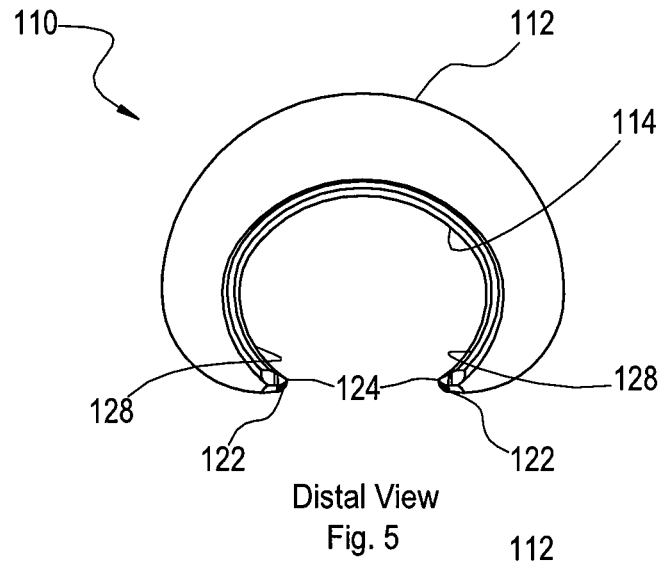
Distal View
Fig. 5
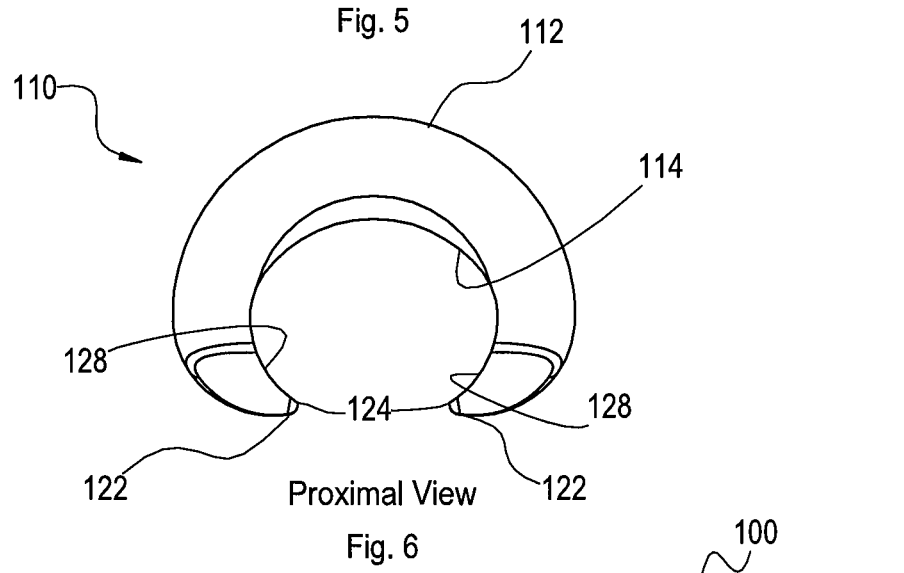
Proximal View
Fig. 6
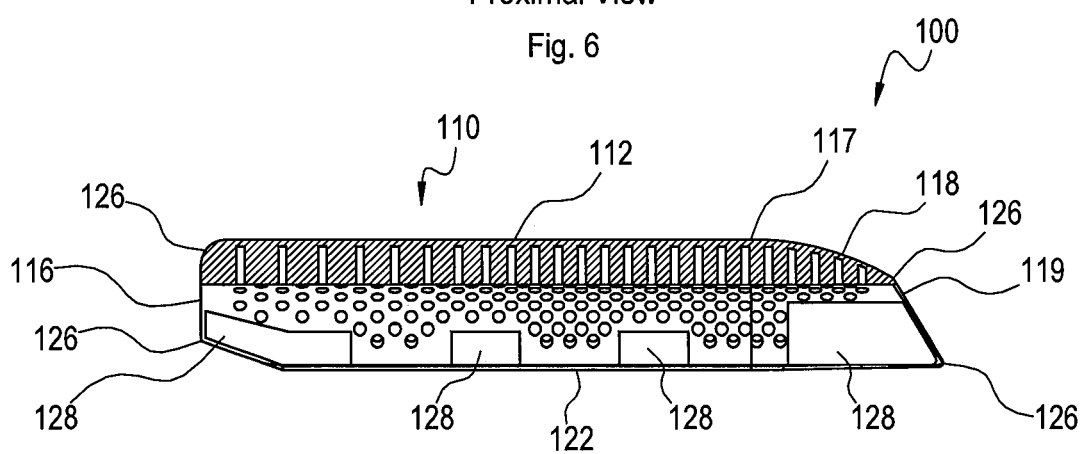
Fig. 7 Section C-C

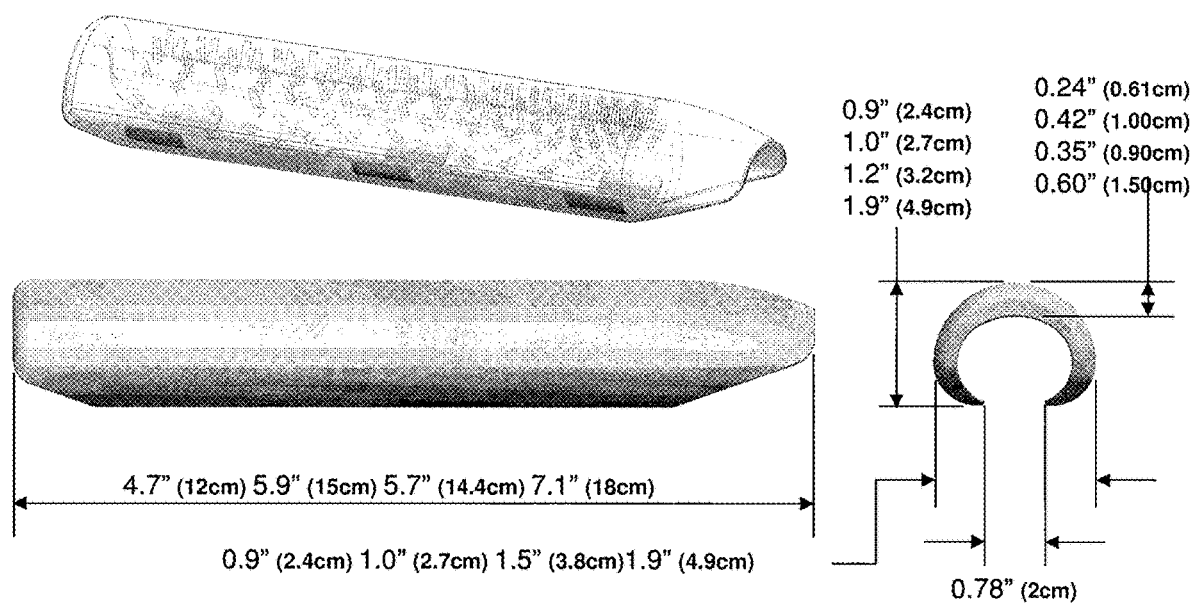
Figure 10 (Large – Extra Large – 2X Large)

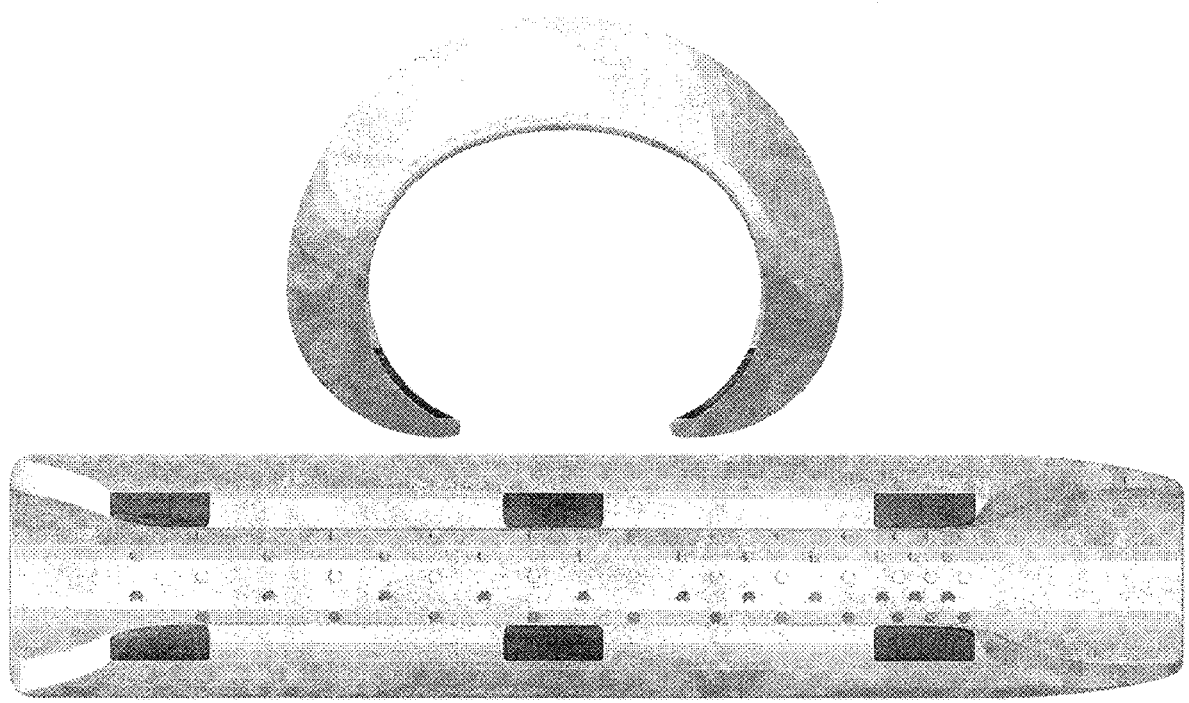
Figure 11 (Mesh Tab Locations)

| Sample Color | Red | White | Blue |
|---|---|---|---|
| Durometer | 0 Type A | 7 Type A | 20 Type A |
| Elongation | 290 psi | 350 psi | 700% |
| Tensile | 1140% | 1000% | 750 psi |
| Tear | 55 ppi | 70 ppi | 125 ppi |

Mesh Material Options

| Mesh | Mfg | Pore Size (mm) | Weight (g/m²) | Filament | Mechanical Properties |
|---|---|---|---|---|---|
| 3D Max | Bard | 0.8 | 80–100 | Monofilament | Tensile 24.7 N/cm |
| Prolite | Atrium | 0.8 | 80–100 | Monofilament | Tensile 38 N/cm |
| Premilene | B-Braun | 0.8 | 80–100 | Monofilament | Tensile 41.4 N/cm |

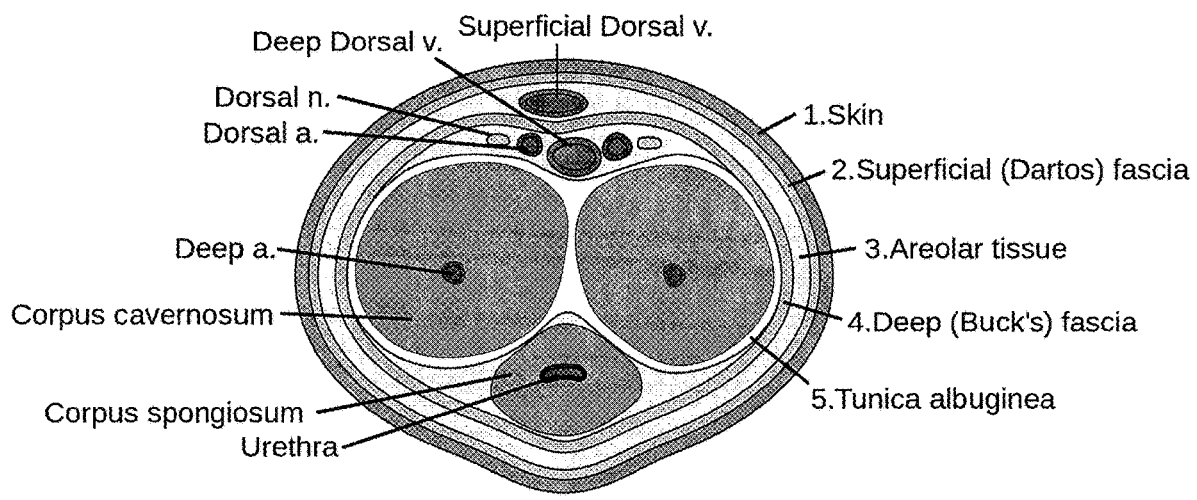
Figure 14A Penile Implant Placement location

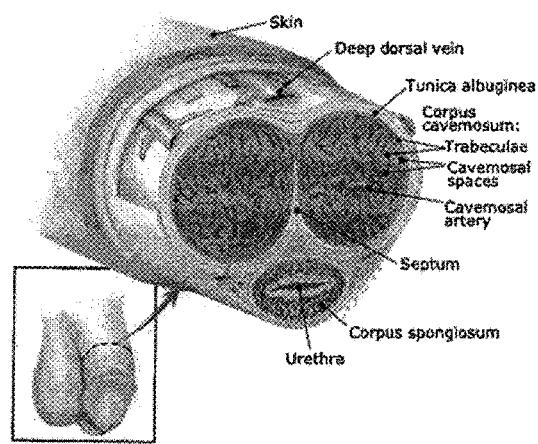
Figure 14B Implantation

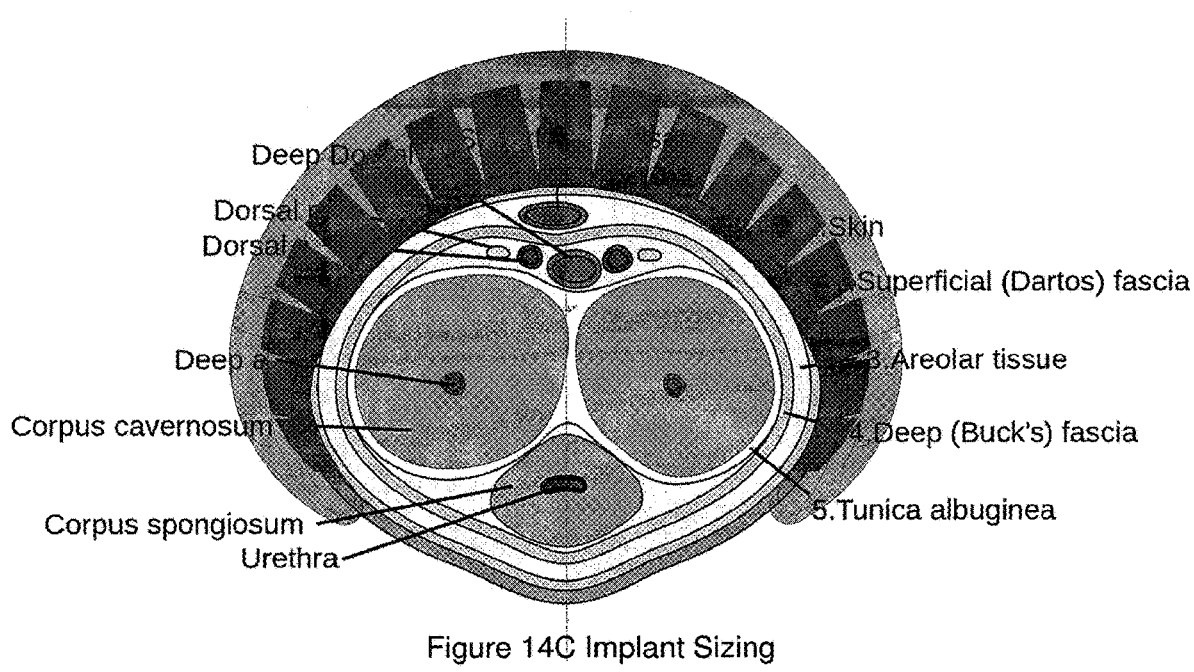
Figure 14C Implant Sizing

US 10,980,639 B2

IMPLANTS THAT FACILITATE TISSUE EXPANSION

CROSS REFERENCE TO RELATED APPLICATIONS

The instant application claims priority to U.S. Ser. No. 62/702,062 filed Jul. 23, 2018 and U.S. Ser. No. 62/779,825 filed Dec. 14, 2018. The aforementioned applications are incorporated by reference for U.S. purposes.

BACKGROUND AND SUMMARY OF INVENTION

Cosmetic implants such as breast implants and penile implants are growing in popularity. Similarly, prosthetic and other medical devices are increasingly employed to treat or ameliorate conditions. For both implants and other medical devices it is often desired that they conform to existing tissue and/or mimic normal anatomical movement such that they resemble the natural human or animal body part or even have an enhanced appearance relative to the natural human or animal body part. Unfortunately, implants and devices made using conventional technology often results in an implant or device which does not facilitate tissue expansion, inhibits normal anatomical movement, and/or does not resemble a natural body party. Thus, what is needed is an implant that accomplishes one or more of the aforementioned desirable characteristics.

Advantageously, the instant invention implants and medical devices overcome the problems described above. The implants typically comprise one or more biocompatible materials. Advantageously, in some embodiments the one or more materials may be selected or configured to facilitate tissue expansion while not substantially inhibiting normal anatomical movement. The implants also may advantageously resemble a natural body party or even have an enhanced appearance relative to a natural body part. Thus, the concepts of the instant invention are applicable to, for example, breast implants, penile implants, testicular implants as well as, incontinence devices such as male or female urethal continence plugs.

The above-described concepts may be particularly useful with respect to cosmetic penile implants because currently available cosmetic penile enhancement devices suffer from a number of limitations and deficiencies. Some comprise a rigid, inelastic silicone block that increases the risk of external erosion, patient discomfort, and an unnatural flaccid penile look and feel. Infection rates are also arguably higher with currently available cosmetic penile implants because none are antibiotic-coated or antimicrobial-resistant. Additionally, the current cosmetic penile implants are implanted using non-absorbable sutures near the dorsal neurovascular bundle distally, risking penile devascularization and denervation that can produce penile necrosis or reduced penile sensation. Further, the rigid silicone block and non-absorbable sutures prevent full penile elasticity during an erection that can reduce potency and cause discomfort during an erection.

Accordingly, in one specific embodiment the instant invention pertains to a penile implant. The penile implant generally comprises a body having outer and inner surfaces and a longitudinal axis and of a selected longitudinal length to be aligned with the long axis of a penis. The body comprises a cross-section perpendicular to the longitudinal axis of the body having a wall thickness that tapers circumferentially in opposite directions beginning from a maximum thickness along a dorsal midline to a minimum thickness along ventral edges that form a ventral opening. Advantageously, the penile implant comprises one or more biocompatible materials selected or configured to facilitate tissue expansion.

The improved cosmetic penile implant of the present invention greatly reduces these untoward complications and provides the patient with a safer, more comfortable, and more natural cosmetic penile enhancement while safeguarding natural penile sexual function. Thus, the cosmetic penile implant implanted subcutaneously may be configured to replicate as nearly as possible the natural human anatomy in shape, appearance, elasticity, compressibility, texture, and feel.

These and other embodiments are described in detail below.

BRIEF DESCRIPTION OF THE DRAWINGS

FIG. 5 illustrates a distal end view of the implant shown in FIG. 1.

FIG. 6 illustrates a proximal end view of the implant shown in FIG. 1.

FIG. 7 illustrates a section view of the implant shown in FIG. 5.

FIG. 10 illustrates various representative dimensions of various size penile implants.

FIG. 11 illustrates representative mesh tab locations for the penile implant shown in FIGS. 9A and 9B.

FIGS. 14A, 14B, and 14C illustrate penile implant location, method, and sizing embodiments.

DETAILED DESCRIPTION OF THE INVENTION

Figure 1:
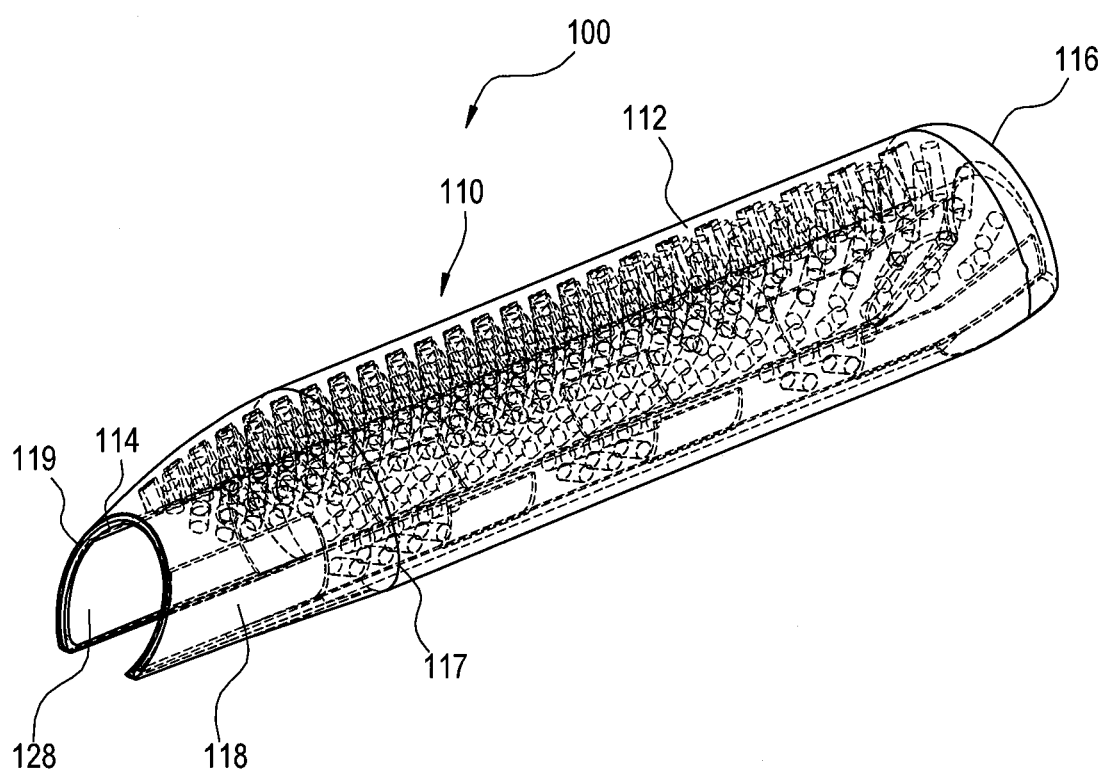
FIG. 1 illustrates a perspective view of an embodiment of a penile implant.

General Implant—Description of Implants Methods of Making, Materials, Configurations, Characteristics (Cosmetic and Physical), Specific Implant Types As described above, the implants and devices of this invention may be suitable for animals or humans. The specific material or materials employed will vary depending upon the specific implant, application, desired characteristics, and the like. In many applications the material employed will be biocompatible, i.e., not particularly harmful to the tissue that is near or in communication with the device or implant whether it be human or animal tissue. The one or more materials are typically selected, configured, or both to facilitate tissue expansion while not substantially inhibiting normal anatomical movement and/or substantially mimicking soft tissue characteristics of the natural body part. Of course, the selected one or more materials and the specific configuration will vary depending upon the specific implant and desired tissue expansion and/or other results.

In one embodiment, to facilitate tissue expansion while not substantially inhibiting normal anatomical movement the implant comprises one or more biocompatible materials selected or configured such that a measured property at a first location on said implant is different than said same measured property at a second location on said implant. Of course, using the present invention a measured property may be different at three or four or any number of locations on the implant. That is, the implant could, for example, exhibit a gradient, i.e., an increase or decrease in the magnitude of a measured property (e.g. hardness (durometer) and other properties such as tensile strength; tear strength; compressive strength; and elongation which also may be referred to as extensibility or stretching or elasticity) that is observed in passing from one point or location on the implant to another. This can be accomplished in at least two general ways or a combination of these two.

First, the material employed may be different at the first, second, and/or other additional locations of the implant. That is, the material or materials employed may vary at the first, second, and/or other locations of the implant with respect to a property of interest for the implant. That is the material or materials of the implant may be different with respect to, for example, one or more, two one or more, three one or more, four one or more, or even five of the following properties: (1) hardness; (2) tensile strength; (3) tear strength; (4) compressive strength; and (5) elongation.

Making an implant having different properties at different locations on the implant may be accomplished in any convenient manner, e.g., by using different material of different properties. Such manners will differ based on the implant, its properties, materials employed, and desired characteristics.

Suitable methods may include molding, e.g., injection molding, extrusion, rotomolding, transfer molding, compression molding, blow molding, 3D printing, and the like. In general, any suitable process may be employed so long as the desired material with the desired property can be placed at the desired locations on and/or within the implant. For example, if using injection molding one might use a mold in the shape of the desired implant. The mold may have multiple injection points, e.g., two or more, three or more, four or more, or up to as many as necessary or desired. In this manner different materials (or the same material with varying properties) may be injected through each injection port. If desired, there may be compartments within the mold but often compartments are unnecessary as factors such as the different injection points and timing of injection may control the ultimate placement of the various materials. In this manner, the implant can be designed or tailored to have different properties at different locations or places on or within the implant. Thus, the desired properties such as (1) hardness; (2) tensile strength; (3) tear strength; (4) compressive strength; and (5) elongation can be tailored throughout the implant by selecting the one or more biocompatible materials such that a measured property at a first location on said implant is different than said same measured property at a second, third, fourth, or even additional locations on said implant.

A second method of making an implant wherein a measured property at a first location on said implant is different than said same measured property at a second or even more locations involves configuring the material within the implant to achieve this. This second method can be used independent of the first method which uses varying materials or a material that varies in properties. Alternatively, the configuring described further below may be done in in conjunction with the use of varying materials or the use of a material that varies in properties.

In some embodiments of this second method, the one or more materials are configured to comprise one or more internal pockets within the implant. Such pockets are void spaces within the implant. The design and configuration of the pockets or void spaces will vary depending upon the type of implant and desired characteristics. For example, the implant geometry, size, depth, and/or location of the pockets can be configured to result in one or more of the following: (1) reduce rigidity of at least a portion of the implant, (2) reduce the total weight of the implant, (3) increase elongation (elasticity or extensibility) of at least a portion of the implant, or (4) increase compressibility of at least a portion of the implant. As a specific example, the internal pockets may comprise pockets to modify the measured compression or elongation at different places on or within the implant, i.e., compression pockets, elongation pockets, or both. In a specific embodiment, the implant may be configured with internal pockets that, for example, permit elongation or stretching. For example, in some embodiments, the implant may be configured with internal pockets such that stretching of at least 10%, or at least 20%, or at least 40%, or at least 60%, or at least 80%, or at least 100%, or at least 150%, or at least 200% occurs compared to the same implant substrate (e.g., same polymer in same shape) without internal pockets. On the other hand, the implant may be configured with internal pockets such that stretching of up to at most 500%, or at most 450%, or at most 400%, or at most 350%, or at most 300%, or at most 250% occurs compared to the same implant substrate (e.g., same polymer in same shape) without internal pockets. By stretching is meant to refer to either elongation in one direction or compression in the other direction.

Figure 15:
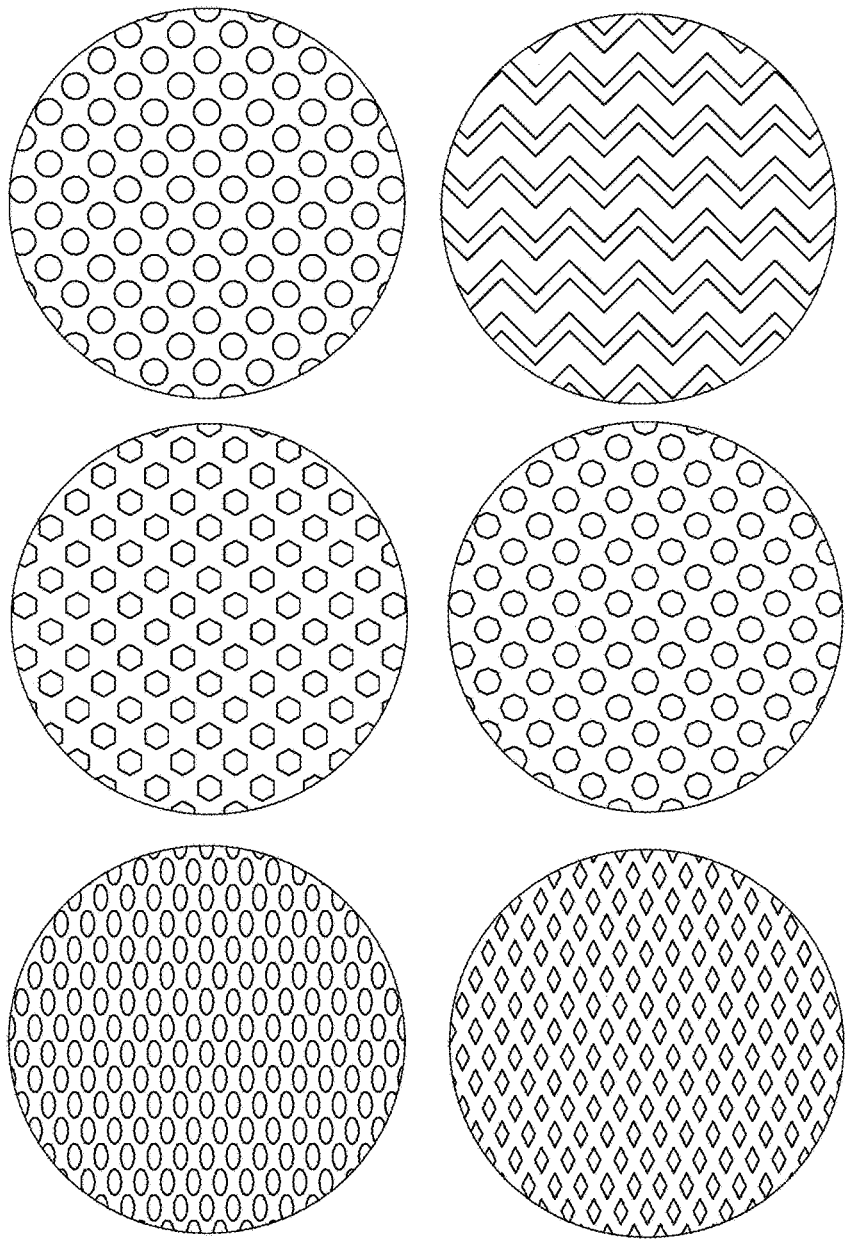
FIG. 15 shows various configurations of the internal pockets of an implant core.

As stated above, the particular geometry of the internal pockets may vary widely depending upon the desired results. In particular embodiments, the implant may be designed such that the internal pockets of the implant may be in a honeycomb (e.g., polygonal such as hexagonal), a zig zag (WWWWW), or even an elliptical configuration. In this manner, the implant can be made such that a measured property at a first location on said implant is different than said same measured property at a second, third, fourth, or even additional locations on said implant. For example, the implant's hardness at a particular location will usually depend at least in part upon the nature and volume of the pockets or voids beneath the location. That is, the greater the volume of voids beneath a particular implant location, the softer the implant may feel at that particular location. Thus, an implant may have a dense honeycomb at the distal end with a less dense honeycomb at the proximal end or a gradient or graduated honeycomb densities leading to different hardnesses and/or other properties over the length and/or various dimensions of the implant. Likewise, the geometry, size, depth, and/or location of the pockets beneath a particular location also affect and/or determine the other properties of the implant beneath that location, e.g., tensile strength; tear strength; compressive strength; and elongation (extensibility or elasticity). In this manner, the configuration of the pockets can be tailored or designed to change the properties at various locations on the implant. FIG. 15 shows various configurations of the internal pockets of an implant core.

The desired configuration of the implant's pockets, if any, may be accomplished in any convenient manner and such manners may differ depending upon the type of implant, material(s) employed, desired properties, and other factors. One way of configuring an implant is through the use of injection molding wherein the mold cavity may include a removable structure in the geometry of the desired pockets so that when structure is removed pockets or voids exist within the molded implant. A commonly used injection molding method using a core, a cavity side A, and a cavity side B may be employed. Dual or multiple extrusion, 3-D printing and other methods may also be used to make the aforementioned implant structures.

The specific material or materials employed for the implants herein are not particularly limited so long as they are typically biocompatible and can be made to have one or more, or two or more, or three or more, or four or more, or all of the desired properties (e.g., hardness, tensile strength; tear strength; compressive strength; and/or elongation) in the desired ranges described herein for the implant. Thermosets, thermoplastics, elastomers, or combinations thereof may be employed. Useful thermoplastics may include nylon, polyethylene, polypropylene, and polystyrene while useful thermosets may include various epoxy resins and phenolic resins in any form while preferred thermosets may include various gel colloids. Silicone and polyurethane may be particularly useful materials for some types of implants. Particularly preferred materials include foams, either solid or semi-solid, closed cell foams such as those comprising urethane, silicone, or mixtures thereof.

Particularly preferred configurations for various implants include those that comprise a wall having a varying wall thickness over one or more dimensions of the implant. Another preferred configuration is one in which the amount of materials employed within the implant are changed over one or more dimensions in a gradient such as by a changing or changed honeycomb structure. By reducing the wall thickness or alternatively having more voids in perhaps a honeycomb structure over the length of the implant the hardness or other properties may be changed such the implant is similar to natural tissue and/or allows normal physiological movement while augmenting the size or otherwise enhancing the appearance of the body part. In another embodiment the implant comprises one or more biocompatible materials having both linear and radial compression capability. This may assist in tissue expansion and may also contribute to the implant being similar to natural tissue and/or allowing normal physiological movement while augmenting the size or otherwise enhancing the appearance of the body part.

The specific properties of the implant may vary depending upon the material(s) employed, their placement, and the configuration, e.g., geometry, size, depth, or location of pockets, if any. In one embodiment the implant comprises one or more biocompatible materials wherein a specific location on the implant and/or the material has a durometer range of from about 0, or from about 10, or from about 20, or from about 30 up to at most about 70, or up to at most 60, or up to at most 50, or up to at most 40 durometer on the Shore A scale according to ASTM D2240-15.

Other useful properties of the implant that may be determined by the material or configured as desired may include elongation, tensile strength, tear strength, compressibility or extensibility. Specifically, useful implant embodiments may comprise wherein the implant comprises one or more biocompatible materials wherein a specific location on the implant and/or the material employed has a tensile strength of from at least about 200 psi, or at least about 300 psi, or at least about 350 psi up to at most about 1000 psi, or up to at most about 800 psi, up to at most about 700 psi, or up to at most 600 psi according to ASTM D412-06. Similarly, the implant may comprise one or more biocompatible materials wherein a specific location on the implant and/or the material employed has an elongation of from at least about 400%, or at least about 500%, or at least about 600%, or at least about 700%, or at least about 800%, up to about 1200%, or up to about 1100%, or up to about 1000% according to ASTM D412-06. Similarly, the implant may comprise one or more biocompatible materials wherein a specific location on the implant and/or the material employed has a tear strength of at least about 40 pounds per inch (ppi), or at least about 50 pounds per inch (ppi), or at least about 60 pounds per inch (ppi), or at least about 70 pounds per inch (ppi), or at least about 80 pounds per inch (ppi), up to about 200 ppi, or up to about 130 ppi, or up to about 120 ppi, or up to about 110 ppi according to ASTM D624. The implants of the present invention may also comprise one or more biocompatible materials wherein a specific location on the implant and/or the material employed has a compressibility and/or extensibility factor of from at least 0, or at least 5, or at least 10, or at least 15, up to about 20, or up to about 25%. Compression can be tested by, for example, ASTM D395-03.

In other embodiments of the instant invention the implants may comprise one or more biocompatible materials wherein a specific location on the implant and/or the material employed has at least one, or at least two, or at least three, or at least four or more of the above-described properties.

The implants may comprise further materials depending upon the desired properties and application. For example, the implant may comprise hydrophilic or hydrophobic agents on the interior or exterior of the implant. In one specific embodiment the implants have a hydrophilic agent on the exterior such that the implant is at least partially resistant to bacteria, viruses, and the like in that they cannot adhere to the surface. Such hydrophilic agents are not particularly limited and depend upon the application. As such they may be selected from any compatible material and applied in suitable amounts to achieve the desired effect.

Other suitable additives to the interior and/or exterior of the implant comprise a material capable of releasing heat and/or a material capable of absorbing heat. In this manner the implant or portions of the implant may be made to be exothermic or endothermic based on exposure to one or more stimuli.

As described above, the instant inventions are widely applicable to any number of types of implants and/or prosthetic or other medical devices. Specific embodiments may be particularly applicable to penile implant, a testicular implant, a female incontinence implant, a breast implant, or similar implants and devices. More specifically, the instant inventions may be particularly applicable to those applications wherein tissue expansion is desired. Such applications include, but are not limited to, e.g., applications wherein desired tissue expansion includes being near a urinary meatus, a fossa navicularis, or a bladder neck when, for example, said implant is intended for or placed in a human. Particularly preferred applications may include, for example, those wherein the implant may be a penile implant, a male or female incontinence implant or plug, or a breast implant. Of course, the method of placing, attaching, inserting, and/or employing the implants of the instant invention will vary depending upon the specific type of implant and the person or animal's anatomy with which it will be employed. In most instances conventional and known surgical techniques or concepts can be employed with a given implant. A specific embodiment pertaining to a cosmetic penile implant is described below.

Specific Penile Implant Embodiments

The following specific embodiments disclosed relate to cosmetic penile implants and method of implanting. However, it should be understood that the concepts, materials, properties, methods of making, and other description above apply equally to cosmetic penile implants. Similarly, the concepts, materials, properties, methods of making, and other description specific to the penile implant embodiment described below may also be applicable to many other types of implants and/or prostheses.

Figure 8:
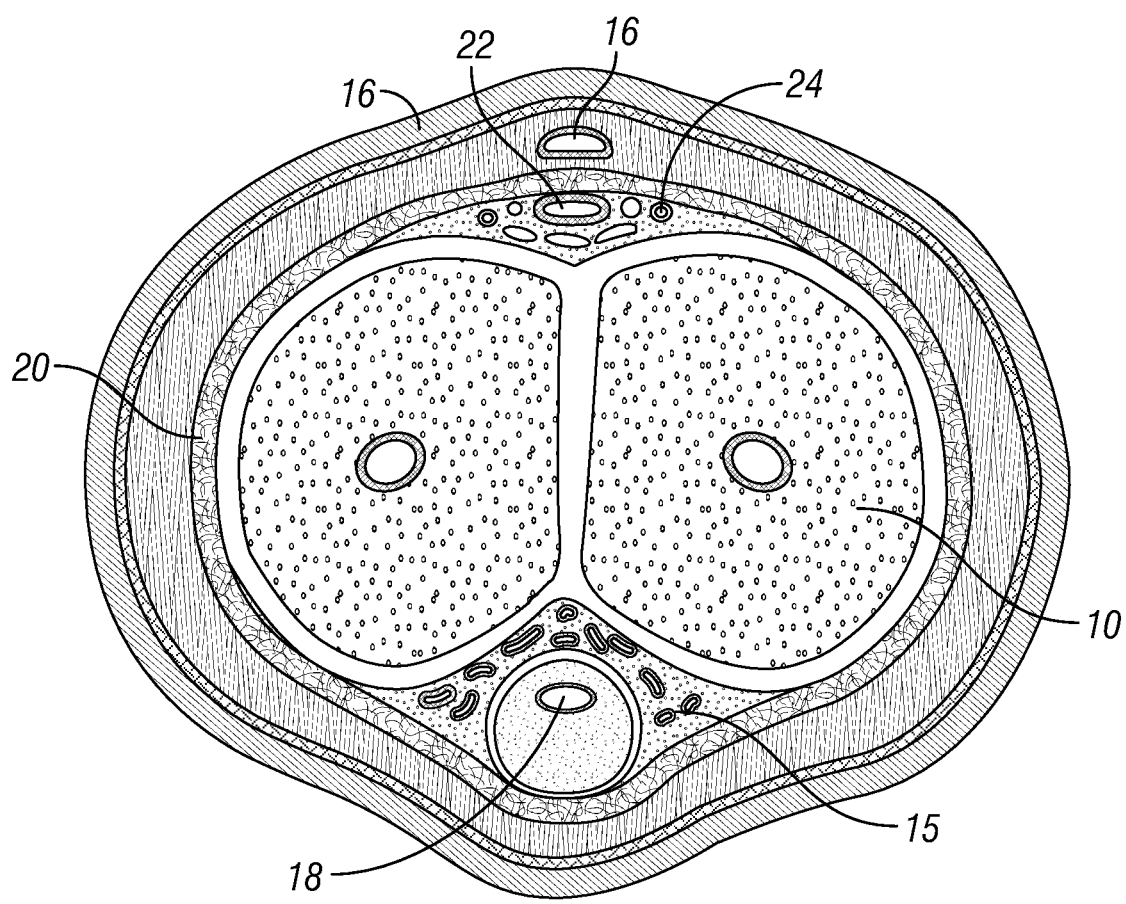
FIG. 8 shows a section of the natural anatomy of a penis.

FIG. 8 illustrates a cross-section of the natural penile anatomy consisting of several distinguishable parts. The glans penis is commonly referred to as the head of the penis. The skin 16 is the outer layer of the penis. The corpus cavernosum 10 are two columns of spongy erectile tissue comprising the dorsum of the penis bilaterally which, when filled with blood, cause an erection. The corpus spongiosum 15 is a column of sponge-like tissue comprising the medial ventrum of the penis surrounding the urethra 18 from the bladder neck to the glans penis which also fills with blood during an erection, but does not contribute to the erection. The paired corpora cavernosa 10 and the corpus spongiosum 15 are enclosed within a tube of deep fascia 20 called Buck's fascia. Buck's fascia 20 also surrounds the deep dorsal vein 22, and the paired dorsal arteries and dorsal nerves 24 of the penis.

The cosmetic penile implant may have a body having a longitudinal axis of a selected longitudinal length to be aligned with the long axis of the penis. The body may have any length and any diameter or width. In one embodiment, the body may have a cylindrical cross section. In other embodiments, the body may have an elliptical or oblong cross section. In yet other embodiments, the body may have a cross section of any shape. The body has an outer surface and an inner surface. The body may be formed as one integral part. A cross-section perpendicular to the longitudinal axis of the body may have a wall thickness that tapers circumferentially in opposite directions beginning from a maximum thickness along a dorsal midline to a minimum thickness along ventral edges that form a ventral opening. The ventral edges may be straight or scalloped edges. The body may be open at both its proximal end (nearest to the base of the penis), as well as the opposite distal end (nearest to the glans penis).

The body may also have a constant wall thickness in a direction extending longitudinally from the body's proximal end to the beginning of a distal portion at which point the wall thickness tapers from the beginning of the distal portion to the body's distal end. A constant wall thickness extending along a longitudinal length of the body from the proximal end to the beginning of the distal portion is preferred over a tapered wall thickness because the constant wall thickness more closely matches the natural anatomy of the penis. The distal portion has a tapered wall thickness only for a short portion near the distal end of the body (nearest the glans penis). The body may have all edges and corners rounded, chamfered, or pillowed. The implant is configured to have a size and shape adapted for subcutaneous implantation between the exterior skin and adjacent Buck's fascia. When implanted the device may extend from the base of the penis at its proximal end to the glans penis at its distal end.

The body may be made of any type of polymer, elastomer, rubber, composite material, or any other spongy or flexible or compressive material that replicates as nearly as possible the natural human anatomy in shape, appearance, elasticity, compressibility, texture, and feel. The implant body material will be as flexible, compliant and compressible to most closely simulate normal penile tissue in a flaccid state while producing enhanced flaccid penile length and girth. In one embodiment, the body may be made of a silicone. In another embodiment, the body may be made of polyurethane. The softness of the material forming the body of the implant may have a Shore A softness of less than 25, or less than 20, or less than 15, or less than 12, or more preferably less than 10. A shore durometer measures hardness of a material, typically of polymers, elastomers, and rubbers. High numbers in its scale indicate a greater resistance to indentation, and thus harder materials. Lower number indicate softer, more compressible or more flexible materials. There are several scales of durometer, used for materials with different properties. The two most common scales, using slightly different measurement systems, are the ASTM D2240 type A and type D scales. The A scale is for softer materials, while the D scale is for harder materials.

If desired, mesh tabs of from about 1 to about 2 cm in length may be placed through the length of the lateral margins spaced from about 0.75 cm to about 1.25 cm apart. The body may have one or more embedded tabs, e.g., mesh tabs, protruding from its proximal end, and one or more embedded mesh tabs protruding from its distal end. The mesh tabs may protrude beyond the proximal end and the distal end up to any distance. For example, the embedded mesh tabs may protrude bilaterally (on both sides) up to 0.5 cm beyond the distal end, or up to 1.0 cm beyond the distal end, or up to 1.5 cm beyond the distal end, or greater. The embedded mesh tabs may protrude bilaterally up 1.0 cm beyond the proximal end, or up to 1.5 cm beyond the proximal end, or up to 2.0 cm beyond the proximal end, or greater. The mesh tabs may be any shape and size, such as, for example, rectangular or square with right angles at edges, and are provided as a functional means for suturing the body at both distal and proximal ends to Buck's fascia and the fibrous tunical sheath of the corpus cavernosa, to support maintaining the body in place and prevent longitudinal and/or rotational migration. The mesh tabs are configured to receive tissue ingrowth and may be made of any material and mesh size that supports and promotes natural tissue ingrowth. For example, the mesh may be polyurethane mesh. Or the mesh may be another other type of material commonly used in reconstructive general, plastic, or urologic surgery as will be understood by one of ordinary skill in the art. Absorbable sutures may be used to fasten the mesh tabs to Buck's fascia and the corpus cavernosa tunic. Suturing will be understood by one of ordinary skill in the art. The mesh tabs may be formed integrally with the body, or embedded within the body, or attached to it, or attached between multiple layers of the body, or attached to the body by other methods of attachment. The mesh tabs are located at the proximal end and the tapered distal end as near the ventral margin as possible. Mesh tabs are not located within or attached to the body along or near the dorsal midline to avoid suturing or tissue ingrowth near the dorsal neurovascular bundle, which would risk denervation or devascularization of the penis both during implantation or during any subsequent required explanation.

The body may have an antimicrobial surface coating that contains an antimicrobial agent that inhibits the ability of microorganisms to grow on the surface of the body. For example, an antibiotic or antibacterial may coat the surface or be embedded into the implant material and thereby potentially reduce the risk of bacterial infections of the implant. In one embodiment, the body may be dipped into an antibiotic or antibacterial agent to coat the surfaces. In another embodiment, the body may be impregnated with an antibiotic or antibacterial agent when the body is formed. The antibiotic coating or impregnation of the body will be consistent with bioprosthesis standards as will be understood by one ordinarily skilled in the art. Any type of antibiotic or antibacterial agent may be used. For example, in certain embodiments, Rifampin and/or Minocycline may be used.

Figure 2:
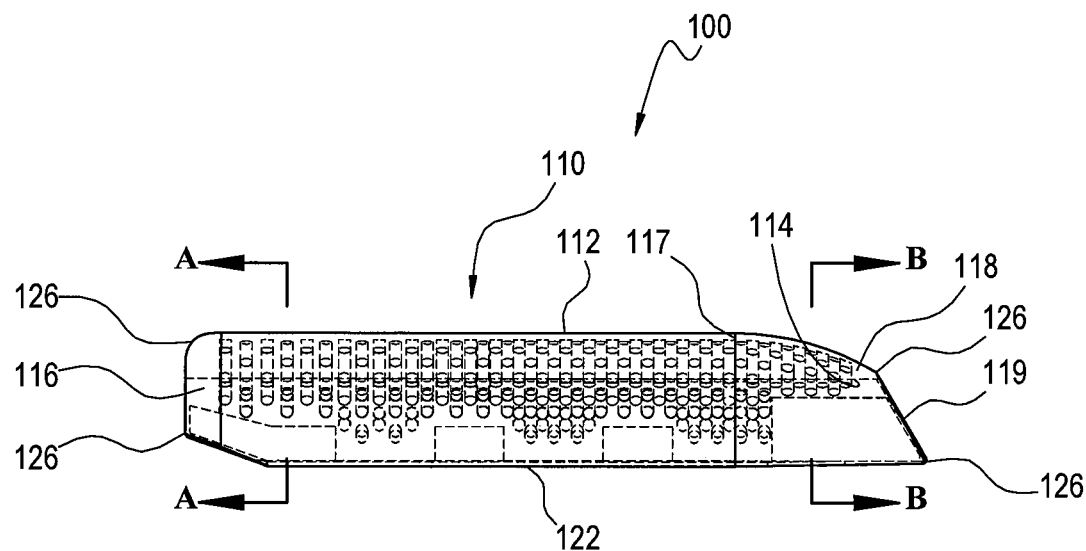
FIG. 2 illustrates a side view of the implant shown in FIG. 1.
Figure 3:
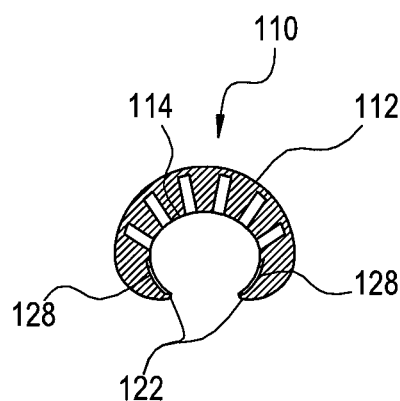
FIG. 3 illustrates a section view of a proximal end of the implant shown in FIG. 2.
Figure 4:
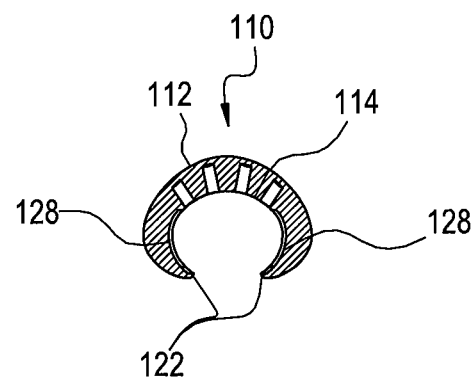
FIG. 4 illustrates a section view of a distal end of the implant shown in FIG. 2.

FIGS. 1-7 illustrate an embodiment of a penile implant 100. FIG. 1 illustrates a perspective view of an embodiment of the penile implant 100. FIGS. 2 and 7 illustrate side and cross section views of the penile implant 100, respectively. The implant 100 has a cylindrical body 110 having a longitudinal axis and of a selected longitudinal length to be aligned with the long axis of the penis. The cylindrical body 110 has an outer cylindrical surface 112 and a smaller inner cylindrical surface 114. FIGS. 3 and 4 illustrate cross-section views perpendicular to the longitudinal axis of the cylindrical body 110. The cylindrical body 110 has a wall thickness that tapers circumferentially in opposite directions beginning from a maximum thickness along a dorsal midline 120 to a minimum thickness along ventral edges 122 that form a ventral opening 124. The ventral edges 122 are illustrated as scalloped, however they may also be straight edges.

FIG. 5 illustrates a distal end view, FIG. 6 illustrates a proximal end view of the penile implant 100. The cylindrical body 110 may be open at both its proximal end 116 (nearest to the base of the penis), as well as the opposite distal end 119 (nearest to the glans penis). The body 110 may also have a constant wall thickness in a direction extending longitudinally from the body's proximal end 116 to the beginning 117 of a distal portion 118 where the wall thickness tapers from the beginning 117 of the distal portion 118 to the distal end 119 of the cylindrical body 110. The distal portion 118 has a tapered wall thickness from the beginning 117 of the distal portion 118 to the distal end 119 of the cylindrical body 110 (nearest the glans penis). The cylindrical body 110 may have pillowed or rounded edges 128 at both the proximal end 116 and the distal end 119. The implant 100 is configured to have a size and shape adapted for subcutaneous implantation between the exterior skin 16 and adjacent to Buck's fascia 20. The implant may extend from the base of the penis at its proximal end to the glans penis at its distal end.

The cylindrical body 110 further includes embedded mesh tabs 128 that are located at its proximal end 116, and one or more embedded mesh tabs 128 that are located at its distal end 119. The mesh tabs 128 are configured to receive tissue ingrowth and provide a functional means for suturing the cylindrical body at both distal 119 and proximal ends 116 to Buck's fascia 20 to keep the cylindrical body 110 in place and prevent longitudinal and/or rotational migration. Absorbable sutures may be used to fasten the mesh tabs to Buck's fascia and the underlying tunic of the corpus cavernosum. The mesh tabs 128 may be formed integrally with or embedded within the cylindrical body 110, or attached to it, or secured between multiple layers of the cylindrical body 110, or secured to the cylindrical body 110 by another other methods of attachment. The mesh tabs 128 are located at the proximal end 116 and distal end 119 as near the ventral edges 122 as possible. Mesh tabs 128 are not located within or attached to the body 110 along or near the dorsal midline to avoid suturing or tissue ingrowth near the dorsal neurovascular bundle 22, 24, which would risk denervation or devascularization of the penis.

The following methods may be used for implanting the cosmetic penile implant. The cosmetic penile implant may be placed through a peno-scrotal or ventral phalloplasty incision without an abdominal incision being made and without associated surgical drain placement. Through a peno-scrotal or ventral phalloplasty incision, Buck's fascia overlying the fibrous tunic of the corpus cavernosa is identified and the soft tissue attachments are released through both blunt and sharp dissection. Care is taken to avoid disruption of Buck's fascia along the dorso-lateral margins of the corpus cavernosa to avoid injury to the underlying penile neurovascular bundle, thereby avoiding risk of penile devascularization or sensory denervation. Through this incision, the glans penis may be retracted caudally, thereby inverting the penile shaft and permitting direct inspection and additional dissection of the distal penile shaft. The distal implant margin containing the mesh tabs may then be secured lateral to the dorsal neurovascular bundle using absorbable sutures, ensuring secure and proper placement of the implant. Similarly, absorbable sutures may be used to secure the proximal margin of the implant ventrally, permitting tissue ingrowth at each position of the implant at all four quadrants. This additionally secures the implant in the desired location and reduces the risk of implant migration, malposition and erosion. This surgical approach also facilitates, through direct inspection, ventral placement of the implant lateral to the urethral margin bilaterally, further ensuring not only proper implant placement, but a more concealed and comfortable tapered lateral implant margin. The wound and the implant can be copiously irrigated with antibiotic solution and hemostasis achieved and confirmed before the subcutaneous tissue is reapproximated, also with absorbable sutures. The peno-scrotal skin is similarly reapproximated with absorbable sutures providing a two-layered closure. The shaft is then loosely wrapped with gauze and elastic adhesive, taking care to avoid penile ischemia. The patient may be discharged the same day following a brief recovery period with instructions to remove the dressing in 24-48 hours. Cleansing of the wound daily may then occur. Avoidance of sexual intercourse is advised until the one month postoperative examination.

Another method of implanting the cosmetic penile implant may be the methods that are taught by U.S. Pat. No. 4,202,530, which is incorporated herein by reference in its entirety.

The inflatable penile implant to correct erectile dysfunction may be subsequently implanted within the corpus cavernosa, deep to the cosmetic penile implant, without meaningful physical alteration to the cosmetic penile implant or compromise of the intended purpose of the cosmetic penile implant. Similarly, placement of the cosmetic penile implant subsequent to placement of an inflatable penile implant is possible with either surgical approach referenced above. Advantageously, there are no restrictions to erection of the penis following cosmetic implant placement given absorbable suture use, elasticity of the implant body and only segmental use of mesh attachments off the dorsal midline neurovascular bundle.

Figure 9A:
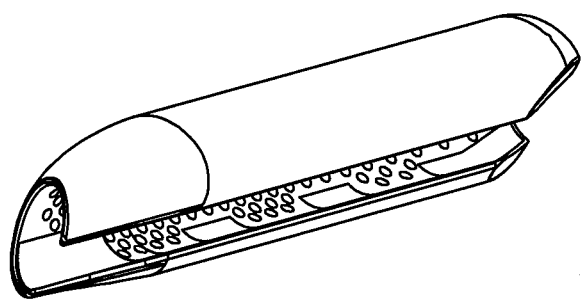
FIGS. 9A and 9B illustrates perspective views of each side of an embodiment of a penile implant.
Figure 9B:
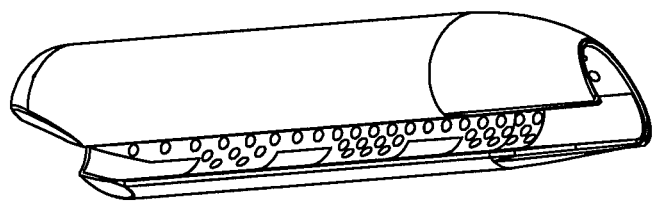

FIGS. 9A and 9B illustrate an embodiment of a penile implant with a perspective view of each side. As shown in FIG. 10 the penile implant, like the other implants herein, can be made in a wide range of sizes and dimensions. Advantageously, the wall thicknesses may vary over the length of the implant and/or the geometry and configuration can be adjusted with pockets as described above. By subtraction of material using thinner walls and/or by adding more pockets, one can change the hardness over the various dimensions of the implant. Thus, the hardness and other properties may change from proximal to distal and vice versa, e.g., the distal portion may have a dense honeycomb structure while the proximal portion is less dense. This assists in, for example, providing augmentation while retaining physiological feel and function. That is, the penile and other implants of the present invention may mimic soft tissue more so than other implants which may, for example, employ a bag-like or balloon like exterior with a cavity filled with fluid-like material. In contrast, the implants of the present invention may be comprised of a single material configured with pockets to adjust the properties.

Figure 13:
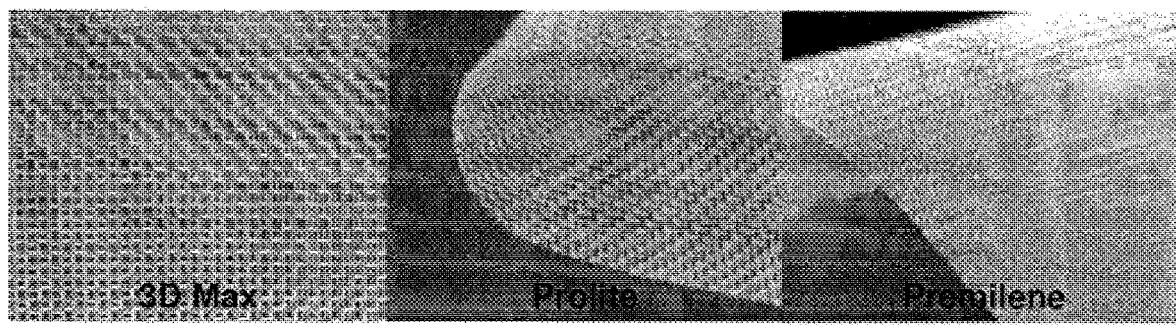
FIG. 13 shows representative mesh material options.

The penile and other implant may be attached in any convenient manner. As described previously in some embodiments the penile implant may comprise tabs for suturing the penile or other implant to the body. If employed, then the tabs may be located at any convenient location and be comprised of any biocompatible material. FIG. 11 illustrates representative mesh tab locations for the penile implant shown in FIGS. 9A and 9B while FIG. 13 shows exemplary types of mesh material that may be employed.

Figure 12:
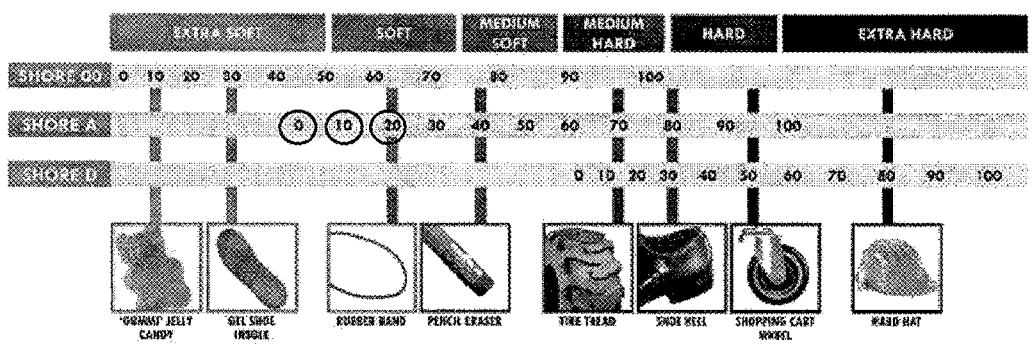
FIG. 12 illustrates Shore Hardness scale and representative properties of various implants.

As described in detail above, the implants, including the penile implant, may be comprised of materials that exhibit various ranges of properties, e.g., durometer, elongation, tensile, tear, etc., at one or more different locations on the implant. FIG. 12 illustrates Shore Hardness scale and representative properties of various implants such as the penile implant. FIGS. 14A, 14B, and 14C illustrate penile implant location, method, and sizing embodiments. If course, if desired one or more of various other features may be incorporated into the penile or other implants so long as they don't substantially interfere with the function. A non-limiting list of such features may include ribs, knobs, horns, grooves, a radiopaque property, fluorescence or some other illuminating property.

The claimed subject matter is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. An implant suitable for a desired animal or human body part or portion thereof wherein the implant comprises an implant body comprising one or more biocompatible materials wherein said one or more materials are selected or configured to facilitate tissue expansion while not substantially inhibiting normal anatomical movement and wherein said one or more biocompatible materials comprise internal pockets of inaccessible enclosed void spaces within the implant body configured such that a measured property of hardness at a first location on said implant is different than said same measured property at a second location on said implant.

2. The implant of claim 1 wherein at least one additional measured property at a first location on said implant is different than said same measured property at a second location on said implant.

3. The implant of claim 2 wherein said additional measured property comprises one or more of the following properties: (1) tensile strength; (2) tear strength; (3) compressive strength; and (4) elongation.

4. The implant of claim 1 wherein said implant comprises one or more biocompatible materials having both linear and radial compression capability.

5. The implant of claim 1 wherein said implant comprises one or more biocompatible materials having a durometer range of from about 0 to about 70 durometer on the Shore A scale.

6. The implant of claim 1 wherein said implant comprises one or more biocompatible materials having a tensile strength of from about 200 psi to about 800 psi.

7. The implant of claim 1 wherein said implant comprises one or more biocompatible materials having an elongation of from about 600% to about 1200%.

8. The implant of claim 1 wherein said implant comprises one or more biocompatible materials having a tear strength of from about 40 pounds per inch (ppi) to about 130 ppi.

9. The implant of claim 1 wherein said implant comprises one or more biocompatible materials having a compressibility and extensibility factor of up to about 25%.

10. The implant of claim 1 wherein said implant comprises one or more biocompatible materials having two or more of the following: (1) a durometer range of from about 0 to about 70 durometer; (2) a tensile strength of from about 200 psi to about 800 psi; an elongation of from about 600% to about 1200%; (3) a tear strength of from about 40 ppi to about 130 ppi; and (4) a compressibility and extensibility factor of up to about 25%.

11. The implant of claim 1 wherein said implant further comprises a hydrophilic agent.

12. The implant of claim 1 wherein said implant comprises a wall having a varying wall thickness.

13. The implant of claim 1 wherein said internal pockets vary in one or more of the following: geometry, size, depth, or location.

14. The implant of claim 13 wherein the said internal pockets are configured to result in one or more of the following: (1) reduce rigidity of at least a portion of the implant, (2) reduce the total weight of the implant, (3) increase elasticity of at least a portion of the implant, (4) increase extensibility of at least a portion of the implant, or (5) increase compressibility of at least a portion of the implant.

15. The implant of claim 13 wherein said internal pockets comprise those selected from compression pockets, elongation pockets, or both.

16. The implant of claim 15 wherein said internal pockets permit stretching of up to 500% compared to the same implant substrate (e.g., same polymer in same shape) without internal pockets.

17. The implant of claim 1 wherein said internal pockets comprise a honeycomb design.

18. The implant of claim 1 wherein said biocompatible material comprises a material that releases heat.

19. The implant of claim 1 wherein said biocompatible material comprises a material that absorbs heat.

20. The implant of claim 1 wherein one or more biocompatible materials have two or more of the following: (1) a durometer range of from about 10 to about 70 durometer; (2) a tensile strength of from about 200 psi to about 800 psi; an elongation of from about 600% to about 1200%; (3) a tear strength of from about 40 ppi to about 130 ppi; and (4) a compressibility and extensibility factor of up to about 25%.

21. The implant of claim 1 wherein the implant is configured in the form of a penis, testicle, or a breast.

22. The implant of claim 1 wherein the implant is configured in the form of a breast.

\* \* \* \* \*